United States Patent [19]

Holden et al.

[11] 4,187,314

[45] Feb. 5, 1980

[54] SUBSTITUTED FURYL-2,3,4,5-TETRAHYDRO-1H-3-BENZAZEPINE COMPOUNDS AND PHARMACEUTICAL USE

[75] Inventors: Kenneth G. Holden, Haddonfield, N.J.; Nelson C. Yim, Philadelphia, Pa.

[73] Assignee: SmithKline Corporation, Philadelphia, Pa.

[21] Appl. No.: 909,073

[22] Filed: May 24, 1978

Related U.S. Application Data

[62] Division of Ser. No. 764,672, Feb. 2, 1977, Pat. No. 4,111,957.

[51] Int. Cl.$^2$ ............... A61K 31/55; C07D 405/04
[52] U.S. Cl. ............... 424/282; 260/340.3; 260/340.5 R; 260/347.2; 260/347.4; 260/347.5; 260/347.7; 424/285
[58] Field of Search ............... 260/347.7, 347.5, 347.4, 260/347.2, 340.5 R, 340.3; 424/282, 285

[56] References Cited

U.S. PATENT DOCUMENTS 3,609,138  9/1971  Mull et al. ............... 260/347.7 X

*Primary Examiner*—Richard Raymond
*Attorney, Agent, or Firm*—William H. Edgerton

[57] ABSTRACT

A group of 7,8-dihydroxy-2,3,4,5-tetrahydro-1H-3-benzazepines with structures containing a furyl ring at position 1 which have dopaminergic activity. Particular species of this group include 7,8-dihydroxy-1-(furyl)-2,3,4,5-tetrahydro-1H-3-benzazepine and its dimethyl ether derivative.

7 Claims, No Drawings

SUBSTITUTED FURYL-2,3,4,5-TETRAHYDRO-1H-3-BENZAZEPINE COMPOUNDS AND PHARMACEUTICAL USE

This is a division of application Ser. No. 764,672, filed Feb. 2, 1977, now U.S. Pat. No. 4,111,957.

This invention comprises a new group of compounds which have structures characterized by being 1-thienyl and 1-furyl-2,3,4,5-tetrahydro-1H-3-benzazepines having two hydroxy substituents in the benz-ring of the benzazepine nucleus. These new compounds have utility as medicinally active compounds especially as cardiovascular agents due to their peripheral dopaminergic activity. They also demonstrate activity in animal tests which are known to predict anti-Parkinsonism activity by means of activity at the central dopamine receptors. Generally speaking therefore they may have both peripheral or central dopaminergic activity.

The structures of the compounds of this invention are specifically identified by having a thienyl or furyl hetero ring at the 1-position of the 2,3,4,5-tetrahydro-1H-3-benzazepine system. Exemplary of this new group of compounds are those represented by the following structural formulas:

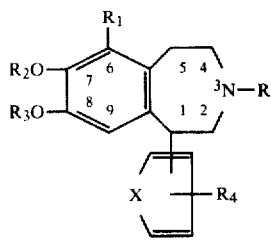

in which:

R is hydrogen, phenethyl, benzyl, lower alkanoyl of from 1–5 carbons such as formyl, acetyl or trifluoroacetyl, lower alkyl of 1–5 carbon atoms, hydroxyethyl or lower alkenyl of 3–5 carbon atoms;

$R_1$ is hydrogen, halo, trifluoromethyl, lower alkylthio such as methylthio or ethylthio, trifluoromethylthio, methyl or methoxy;

$R_2$ and $R_3$ are each hydrogen, lower alkyl of 1–5 carbon atoms, lower alkanoyl of 2–5 carbon atoms or, when taken together, methylene or ethylene;

$R_4$ is hydrogen, halo such as F, Cl or Br, cyano-methyl, carbomethoxy or methyl and X is —O— or —S—.

In the above structural formulas those skilled in the art will recognize that the hetero ring is attached at its 2' (α) or 3' (β) position. The substituents on the two hetero rings are merely limited by the constraints of furan or thiophene chemistry but are of course C-attached.

The thienyl containing congeners are preferred. The furyl congeners may be less active and more toxic than their thienyl counterparts.

A subgeneric group of compounds within the above illustrative generic group are those of Formula I in which:

R is hydrogen or methyl;
$R_1$ is hydrogen or chloro;
$R_2$ and $R_3$ are the same and are hydrogen, methyl or acetyl;
$R_4$ is hydrogen or methyl; and
X is —S—.

The compounds of this invention may also have a fourth benz substituent such as the 9 position but these have not yet been shown to have any particular advantage from the viewpoint of their biological utility. The compounds in which $R_2$ and $R_3$ are higher alkyl or alkanoyl groups or form an alkylene chain such as the methylenedioxy-containing compounds at the 7,8-positions as well as the N-benzyl, phenethyl or alkanoyl containing congeners are of primary interest as intermediates. Methylenedioxy-3-benzazepines in another series are reported in U.S. Pat. No. 3,795,683.

The pharmaceutically acceptable acid addition salts having the utility of the free bases of formula I, prepared by methods well known to the art, are formed with both inorganic or organic acids, for example: maleic, fumaric, benzoic, ascorbic, pamoic, succinic, bis-methylene-salicylic, methanesulfonic, ethanedisulfonic, acetic, oxalic, propionic, tartaric, salicylic, citric, gluconic, aspartic, stearic, palmitic, itaconic, glycolic, p-aminobenzoic, glutamic, benzenesulfonic, hydrochloric, hydrobromic, sulfuric, cyclohexylsulfamic, phosphoric and nitric acids. Similarly the quarternary salts include those prepared from organic halides such as methyl iodide, ethyl iodide or benzyl chloride, methyl tosylate or mesylate which read at the basic 3-center or at a reactive thio center. While the 1-furylbenzazepines form salts readily with strong mineral acids such as sulfuric or hydrochloric acid, such salts are less stable and hard to purify. Therefore the furyl containing compounds are best used either as the base or as a salt with an organic or weak inorganic acid.

Certain 1-phenyl-2,3,4,5-tetrahydro-1H-3-benzazepines have been described in U.S. Pat. No. 3,393,192; British Pat. No. 1,118,688; and Swiss Pat. No. 555,831, including general methods of preparation. However these references disclose no 1-heterosubstituted compounds.

It will be obvious to one skilled in the art that the compounds of Formula I may be present as diastereoisomers which may be resolved into d or l optical isomers. Resolution of the optical isomers may be conveniently accomplished by fractional crystallization of the salts of the base form or of solid derivatives thereof with optically active acids from appropriate solvents. Unless otherwise specified herein or in the claims, it is intended to include all isomers, whether separated or mixtures thereof. Where isomers are separated, the desired pharmacological activity will usually predominate in one of the isomers, most often in the d-isomer.

The compounds of Formula I in which R is hydrogen are generally prepared from intermediates of the following formula:

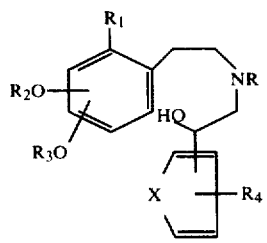

in which R is hydrogen, lower alkyl, benzyl or lower alkenyl; $R_1$ and X are as defined above; $R_2$ and $R_3$ are lower alkyl or together are lower alkylene; and R₄ is hydrogen or a chemically inert substituent of the group described above, by means of an intramolecular cyclization effected by reaction with a reagent such as sulfuric acid alone or mixed with suitable solvents such as trifluoroacetic acid, polyphosphoric acid or a similar dehydrating agent.

Mixed alkoxy substituted compounds are prepared by selecting the proper heteroarylethylamine starting material.

The cyclization is best run to form the methylenedioxy or dimethoxy ethers, then these ether groups are optionally taken off using a mild splitting agent such as boron trichloride for the methylenedioxy or tribromide for the dimethoxy ether.

The heteroarylethylamines (IV) which are used as starting materials for this method are either known or are prepared by methods similar to those disclosed in the illustrative examples.

The 6-substituted compounds are alternatively prepared by oxidizing a 7,8-dihydroxy-1-(furyl or thienyl)-2,3,4,5-tetrahydro-1H-3-benzazepine with 2,3-dichloro-5,6-dicyano-1,4-benzoquinone or similar hydroquinone-oxidizing agent to form the 7,8-dione. This is then reacted with a quinone additive agent, a neucleophic reagent, such as methyl mercaptan, trifluoromethyl mercaptan, hydrogen chloride or hydrogen bromide (in the case where no acid sensitive centers are present) in methanol at about room temperature to give the desired 6-substituted compound.

The 6-bromo containing compound may optionally serve as an intermediate in a number of ways such as for preparing the 6-chloro or 6-iodo congeners or the 6-lithium intermediates. The latter lithium compounds can be reacted with a number of other conventional reactants to introduce 6-substituents such as with iodine or hexachloroethane to introduce iodo or chloro.

To prepare the compounds of Formula I where R is hydroxyethyl, lower alkyl or lower alkenyl, the corresponding benzazepines wherein R is hydrogen are alkylated by standard methods with ethylene oxide, a reactive lower alkyl halide such as the bromide or chloride or a reactive alkenyl halide such as an allyl bromide or chloride. Advantageously, to obtain the products where R₂ and/or R₃ are hydrogen the reaction with the alkylating agent is carried out on the corresponding methoxy substituted benzazepines in an inert solvent such as methanol or acetone, preferably at reflux temperature and in the presence of a basic condensing agent such as potassium hydroxide or carbonate. Treatment of the resulting product with, for example boron tribromide or other ether splitting agents gives the active hydroxy substituted benzazepines. If a reactive center such as a methylthio group is present the sulfonium quarternary salt is prepared. This may be optionally converted back to the methylthio by heating in brine, 1 N hydrobromic acid or another source of halide ions. The 3-methyl congeners are an important part of this invention.

The compounds of Formula I where R is methyl are conveniently prepared from 7,8-dimethoxy substituted benzazepines wherein R is hydrogen by reaction with formic acid/formaldehyde. Treatment of the resulting product with boron tribromide gives the corresponding 7,8-dihydroxy substituted benzazepines. Another method for preparing the important N-methyl compounds is converting the 3-hydrogen compound into the N-formyl congener then reducing with lithium aluminum hydride, a two step reaction sequence.

The dialkanoyloxy derivatives such as the important 7,8-diacetoxy compounds can also be prepared by direct O-acylation of the dihydroxy compound having the N-position blocked by protonation such as using the 6-halo-7,8-dihydroxy-1-phenyl-2,3,4,5-tetrahydro-1H-3-benzazepine hydrobromide in trifluoroacetic acid at ambient temperature with the anhydride or halide. The N or 3-lower alkanoyl congeners in the dihydroxy series are prepared conveniently by N-acylating the methoxy or methylenedioxy derivative followed by splitting the protective group with boron tribromide or chloride. Also direct N-alkanoylation of the dihydroxy compounds is possible under controlled conditions and quantities of reactants as known to the art. As noted in the illustrative examples any undesired O-acylation may necessitate a mild hydrolysis treatment.

The intermediates of Formula III above are conveniently prepared by heating equimolar amounts of an epoxyethylthiophene or furan with a 3,4-dialkoxyphenethylamine which is either known or prepared by methods known to the art, each appropriately substituted, either alone or in an inert organic solvent such as tetrahydrofuran. Preferably the heating is effected on a steam bath or at reflux temperature for from 12 to 24 hours. The required ethylene oxide is conveniently prepared by reaction of the hetero aldehyde with sodium hydride/trimethylsulfonium iodide.

The compounds of this invention can also be conveniently prepared by a process we believe is unique in the benzazepine series as illustrated by the following:

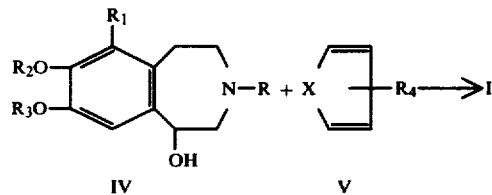

The 1-hydroxy-2,3,4,5-tetrahydro-1H-3-benzazepines of Formula IV are reacted with compounds (V) in which R–R₄ and X are as defined above. As one skilled in the art will recognize certain compounds such as thiophene will react at the position adjacent to the hetero ring member unless that position is occupied. For example the method works nicely to prepare 2'-thienyl compounds. The reaction can also be run to obtain mixtures of mono and poly substituted products which can be separated by methods known to the art. If one or both the α-positions on the heterocycle are occupied, reaction proceeds either in the remaining α or on to the β-position.

The reaction can also be run using IV and in place of a heterocyclic V using benzene having activating groups such as phenol or anisole to produce substituted 1-phenylbenzazepines. R–R₄ are as defined above but for convenience the reaction is usually run on the 1-hydroxybenzazepines in the form of the diether (for example, R₂, R₃=methyl or, together, methylene) with or without the N or 3-position protected such as N-protective groups known to the art, for example benzyl or carbobenzoxy to prepare the 3-hydrogen compounds.

The reaction is run at ambient temperature such as at room temperature for convenient periods of time such as from 1-24 hours. Overnight at room temperature is a convenient laboratory time period. The solvent may be any inert organic solvent or an excess of an organic acid solvent in which the reactants are soluble for example trifluoroacetic acid, methylene chloride, trichloroethylene, chloroform or carbon tetrachloride. Also at least one equivalent of acid catalyst must be present such as trifluoroacetic acid, sulfuric acid, boron trifluoroetherate, etc. Certain 1-hydroxy or alkoxy benzazepines are known to the art such as G. Hazebroucq, Compt. Rend. 257, 923 (1963) [C.A. 59, 12759] or J. Likforman, Compt. Rend. 268, 2340 (1969) [C.A. 71, 61184]. However, the specific 1-hydroxy-7,8-dihydroxy-benzazepine starting materials used here are new and are prepared by methods disclosed in the examples.

The active dopaminergic compounds of this invention used herein stimulate peripheral dopamine receptors, for example they increase renal blood flow and have as an end result hypotensive activity. This renal vasodilator activity of the benzazepine compounds of Formula I is measured in an anesthetized dog. In this pharmacological procedure, a test compound is administered at progressively increasing (3-fold) infusion rates beginning at 0.1 mcg/kg/min up to 810 mcg/kg/min for 5 minutes each to anesthetized normotensive dogs and the following parameters are measured: renal artery blood flow, iliac artery blood flow, arterial blood pressure and heart rate. Results are reported as a percent change, increase or decrease, at time of peak response (from pre-drug controls), and for a significant effect renal blood flow (increase) and renal vascular resistance (decrease) should be approximately 10% or greater. The effect on renal vascular resistance can be calculated from any change in renal blood flow and arterial blood pressure. To confirm the mechanism of action, representative active renal vasodilator compounds are checked for blockade by bulbocapnine which is known to be a specific blocker of renal dopamine receptors. Representative of compounds of Formula I for example: 7,8-dihydroxy-1-(2'-thienyl)-2,3,4,5-tetrahydro-1H-3-benzazepine hydrobromide tested by i.v. infusion as described above produced a decrease of renal vascular resistance of 30% at 30 mcg/kg; 7,8-dimethoxy-1-(5'-methyl-2'-thienyl)-2,3,4,5-tetrahydro-1H-3-benzazepine hydrochloride had an $ED_{15}$ of 2.3 mcg/kg; 7,8-dihydroxy-1-(3'-thienyl)-2,3,4,5-tetrahydro-1H-3-benzazepine hydrobromide had an $ED_{15}$ of 40; the 5-methyl-2-thienyl, 50. $ED_{15}$ therefore is the cumulative dose by infusion which produces a 15% decrease in renal vascular resistance $$(R = \frac{B.P. \text{ in mm/hg}}{B.F. \text{ ml/min}}).$$

In addition to the renal vasodilator activity via a dopaminergic effect, certain benzazepine compounds of Formula I have demonstrated weak diuretic activity. Such diuretic activity is measured in the standard saline-loaded rat procedure. A test compound is administered i.p. at doses of from 10 to 40 mg/kg and the parameters measured are urine volume (hourly for three hours) plus sodium and potassium ion concentrations. Also conventional diuretic tests in the dog may be used. 7,8-Dihydroxy-1-(2-thienyl)-2,3,4,5-tetrahydro-1H-3-benzazepine hydrobromide tested in the phosphate mannitol dog produced a significant increase in renal plasma flow and natriuresis at a dose as low as 10 and 20 μg/kg/min i.v. Similar results were obtained at oral doses of 20 mg/kg.

The benzazepine compounds of Formula I also have some antiparkinsonism activity due to central dopaminergic activity as demonstrated by employing a modified standard animal pharmacological test procedure reported by Ungerstedt et al., in *Brain Research* 24, 1970, 485–493. This procedure is based on a drug induced rotation of rats having extensive unilateral lesions of the substantia nigra. Briefly, the test comprises the quantitative recording of rotational behavior in rats in which 6-hydroxydopamine lesions of the nigrostriatal dopamine system have been produced. A unilateral brain lesion in the left substantia nigra causes the dopamine receptor in the left caudate to become hypersensitive following the resulting degeneration of the nigral cell bodies. These lesions destroy the source of the neurotransmitter dopamine in the caudate but leave the caudate cell bodies and their dopamine receptors intact. Activation of these receptors by drugs which produce contralateral rotation, with respect to the lesioned side of the brain, is used as a measure of central dopaminergic activity of the drug.

Compounds which are known to be clinically effective in controlling parkinsonism, such as, for example, L-dopa and apomorphine, are also effective in the rate turning model. These compounds directly activate the dopamine receptors and cause contralateral rotation of the lesioned rat.

Rotational activity is defined as the ability of a compound to produce 500 contralateral rotations during a two-hour period after administration, usually intraperitoneally. The dose corresponding to 500 contralateral rotations per two hours is obtained and assigned as the $RD_{500}$ value.

Once again representative compounds of Formula I, 7,8-dihydroxy-1-(2'-thienyl)-2,3,4,5-tetrahydro-1H-3-benzazepine hydrobromide, the 3'-thienyl and the 5'-methyl-3'-thienyl congeners when tested as described above in rats produced activity, i.p. at 5.5 ($ED_{500}$), 5 (active) and 1.5 ($ED_{500}$) mg/kg respectively. Further the compounds have a low potential for inducing emesis or sterotyped behavior at doses which are effective in the rat turning model.

The pharmaceutical compositions of this invention having dopaminergic activity are prepared in conventional dosage unit forms by incorporating a compound of Formula I, an isomer or a pharmaceutically acceptable addition of salt thereof, with a nontoxic pharmaceutical carrier according to accepted procedures in a nontoxic amount sufficient to produce the desired pharmacodynamic activity in a subject, animal or human. Preferably the compositions will contain the active ingredient in an active but nontoxic amount selected from about 25 mg to about 500 mg of active ingredient per dosage unit but this quantity depends on the specific biological activity desired and the conditions of patient. Generally speaking lower doses are needed to stimulate central dopamine receptors than peripheral receptors. The dosage units are given from 1–5 times daily.

The pharmaceutical carrier employed may be, for example, either a solid or liquid. Exemplary of solid carriers are lactose, terra alba, sucrose, talc, gelatin, agar, pectin, acacia, magnesium stearate, stearic acid, and the like. Exemplary of liquid carriers are syrup, peanut oil, olive oil, water and the like. Similarly the carrier or diluent may include any time delay material well known to the art, such as glyceryl monostearate or glyceryl distearate alone or with a wax.

A wide variety of pharmaceutical forms can be employed. Thus, if a solid carrier for oral administration is used the preparation can be tableted, placed in a hard gelatin capsule in powder or pellet form, or in the form of a troche or lozenge. The amount of solid carrier will vary widely but preferably will be from about 25 mg to about 1 g. If a liquid carrier is used, the preparation will be in the form of a syrup, emulsion, soft gelatin capsule, sterile injectable liquid such as an ampul, or an aqueous or nonaqueous liquid suspension.

The pharmaceutical preparations are made following the conventional techniques of the pharmaceutical chemist involving mixing, granulating and compressing when necessary, or variously mixing and dissolving the ingredients as appropriate to give the desired end product.

The method of producing dopaminergic activity in accordance with this invention comprises administering internally to a subject in need of such activity a compound of Formula I or a pharmaceutically acceptable acid addition salt thereof, usually combined with a pharmaceutical carrier, in a nontoxic amount sufficient to produce said activity as described above. The route of administration may be any route which effectively transports the active compound to the dopamine receptors which are to be stimulated such as orally or parenterally, the oral route being preferred. Advantageously, equal doses will be administered several times such as two or three times a day with the daily dosage regimen being selected from about 50 mg to about 2 g. When the method described above is carried out hypotensive, diuretic or antiparkinsonism activity is produced with a minimum of side effects.

The following examples are designed solely to illustrate the preparation and use of the compounds of this invention. The temperatures are Centigrade. Other variations of these examples will be obvious to those skilled in the art.

EXAMPLE 1

4.84 Grams of sodium hydride (57% of mineral oil dispersion), after being washed with hexane to remove the oil, was stirred in 70 ml of dry dimethylsulfoxide and heated to 65°–68° under argon for 1 hour. At this point a greenish clear solution resulted. The heating source was removed and 75 ml of dried tetrahydrofuran was then added. The resulting solution was cooled to 5° by means of a methanol-ice bath, and 19 g (93 mmoles) of trimethylsulfonium iodide in 100 ml dry dimethylsulfoxide was added in about 5 minutes. The reaction mixture was stirred for another 5 minutes after complete addition.

A solution of 10.4 grams (93 mmoles) of 2-thiophenecarboxaldehyde in 120 ml of tetrahydrofuran was added to a moderate rate while keeping the reaction mixture at 0° to −5°. The mixture was stirred for another 5 minutes after complete addition and at room temperature for 1 hour, the mixture was diluted with 500 ml of ice water and extracted four times with ether. The combined extracts were washed with saturated brine solution and dried. Removal of the drying agent and solvent gave 10.1 of crude 2-epoxyethylthiophene (yellowish liquid), which was distilled under vacuum to give 8.1 g (69%) of light yellow liquid (b.p. 0.15 mm, 43°–5°).

A mixture of 11.6 g (64 mmoles) of homoveratrylamine and 8.1 g (64 mmoles) of 2-epoxyethylthiophene was heated with stirring and under argon at 100° overnight. The reaction mixture was cooled to room temperature and was chromatographed in a silica column (700 g) and eluted with benzene-ethyl acetate gradient. The desired product and its isomer were thus separated. After recrystallization from ethyl acetate/hexane, 3.6 g (18.4%) of pure N-($\beta$-hydroxy-$\beta$-2-thienyl)ethyl homoveratrylamine was obtained (m.p. 102°).

$C_{16}H_{21}NO_3S$. Calculated: 62.51% C; 6.89% H; 4.56% N. Found: 62.36% C; 6.69 H; 4.51% N.

3.6 Grams (11.8 mmoles) of N-($\beta$-hydroxy-$\beta$-2-thienyl)ethylhomoveratrylamine was dissolved in a mixture of 36 ml of acetic acid and 18 ml of conc. hydrochloric acid. The resulting solution was heated at reflux for 3 hours. The reaction mixture was evaporated under reduced pressure to a brown residue which was then suspended in 5% sodium carbonate solution and thoroughly extracted with ethyl acetate. The extracts were combined, washed once with saturated brine, and dried. Removal of the drying agent and solvent gave 3.3 g of a thick oily residue (96% yield); 1-(2'-thienyl)-7,8-dimethoxy-2,3,4,5-tetrahydro-1H-3-benzazepine.

The procedure outlined above is the basic method for preparing the compounds of this invention. Others may be prepared by substituting equivalent amounts of the appropriate heterocyclic carboxaldehyde or ethylepoxide for the 2'-thienyl reactants in the reactions detailed.

This compound is also prepared by treatment of 8.9 g (40 mmoles) of 1-hydroxy-7,8-dimethoxy-2,3,4,5-tetrahydro-1H-3-benzazepine with 5 ml of thiophene in 45 ml of trifluoroacetic acid under argon at room temperature overnight. After stripping off the volatiles, the residue was dissolved in 250 ml 3 N hydrochloric acid. This acidic solution was thoroughly washed with ether, basified with conc. ammonium, extracted 3 times with ethyl acetate. The extracts were combined, washed once with saturated brine and dried anhydrous potassium carbonate. Removal of drying agent and solvent gave 9.2 of the desired base as an oily residue (81%).

As sample of this oily residue was dissolved in ethyl ether and ethereal hydrogen bromide was added. An off-white precipitate was obtained. This was recrystallized from methanol-ethyl acetate to give the pure hydrobromide (m.p. 215°).

$C_{16}H_{19}SO_2S \cdot HBr$. Calculated: 51.90% C, 5.44% H, 3.78% N. Found: 52.10% C; 5.58% H; 3.65% N.

EXAMPLE 2

3.5 Grams (12 mmoles) of 1-(2'-thienyl)-7,8-dimethoxy-2,3,4,5-tetrahydro-1H-3-benzazepine dissolved in 60 ml of methylene chloride was cooled to −12° by means of a methanol-ice bath, and 6 ml (62 mmoles) boron tribromide was added dropwise. The resulting solution was stirred at room temperature for 1.5 hours and was then evaporated to a brown residue under reduced pressure. The residue was cooled in ice and treated slowly with methanol. The methanol was evaporated at room temperature under reduced pressure. The residue was treated with methanol again and stripped under reduced pressure in a 50° hot-water bath. This treatment was repeated 3 times. The final residue was either chromatographed on a silica column eluted with 9:1 chloroform/methanol or dissolved in water, any undissolved material filtered off and the aqueous filtrate lyophilized to give pure 1-(2'-thienyl)-7,8-dihydroxy-2,3,4,5-tetrahydro-3-1H-benzazepine hydrobromide salt, m.p. 239°–40° (dec), ca. 70% yield.

$C_{14}H_{15}NO_2S \cdot HBr$. Calculated: 49.13% C; 4.71% H; 4.09% N; 9.37% S. Found: 48.91% C; 4.59% H; 4.10% N; 9.10% S.

The free base is obtained by dissolving the salt in a minimum amount of water and slowly adding 5% sodium bicarbonate solution until the base separates.

EXAMPLE 3

3-Thiophenecarboxaldehyde was prepared by following a literature procedure (Org. Syn. Coll. Vol. IV pp. 918-9) from 3-thenyl bromide which in turn was prepared also by following a literature procedure (Org. Syn. Coll. Vol. IV, pp 921-3) from 3-methylthiophene.

11.7 Grams (0.28 mole) of sodium hydride (57% of mineral oil dispersion having been washed with hexane to remove the oil) was stirred in dry dimethylsulfoxide (196 ml) at 60°-65° for 2 hours under argon. The mixture was diluted with dry tetrahydrofuran (196 ml), cooled to −5° and trimethylsulfonium iodide (57.12 g, 0.28 moles) in 196 ml of dry dimethylsulfoxide was added at such a rate that the temperature of the reaction mixture did not exceed 0°. After stirring for another minute after complete addition, 3-thiophenecarboxaldehyde (13.4 g, 0.12 moles) in 84 ml of tetrahydrofuran was added. The methanol/ice bath was removed and the reaction mixture was allowed to warm to room temperature for 1.5 hours, then diluted with 1.1 of ice water and extracted throughly with ether. The extracts were combined, washed with saturated sodium chloride solution and dried with anhydrous sodium sulfate. Removal of the drying agent and solvent gave 16.5 g crude 3-epoxyethylthiophene. Since spectral data (ir, nmr) were satisfactory the epoxide was used without further purification.

A mixture of 39.8 g (0.22 moles) of homoveratrylamine and 24.8 g (0.195 moles) of 3-epoxyethylthiophene was heated with stirring at 100° overnight. The reaction mixture was cooled to room temperature and stirred with 5% ethyl acetate in petroleum ether. The solution was decanted and the crystals were washed twice more with the same solvent mixture to give N-($\beta$-hydroxy-$\beta$-3'-thienyl)ethylhomoveratrylamine. After recrystallization from ethyl acetate, 21.5 g of pure product was obtained, m.p. 113°-4° (36% yield).

$C_{16}H_{21}NO_3S$. Calculated: 62.51% C; 6.89% H; 4.56% N. Found: 61.87% C; 6.92% H; 4.65% N.

9.2 Grams (30 mmoles) N-($\beta$-hydroxy-$\beta$-3-thienyl)ethylhomoveratrylamine was dissolved in 92 ml of acetic acid and 46 ml of conc. hydrochloric acid. The mixture was heated at reflux for 3 hours, stripped under reduced pressure to a brown residue, which was then treated with 5% carbonate solution and thoroughly extracted with ethyl acetate. The organic extracts were combined and washed twice with brine and dried over anhydrous sodium sulfate. Removal of drying agent and solvent gave 8.7 g of thick oily residue (99% yield), 1-(3'-thienyl)-7,8-dimethoxy-2,3,4,5-tetrahydro-1H-3-benzazepine.

A sample of this free base was dissolved in methanol and ethereal hydrogen chloride was added until acidic. This acidic solution was evaporated to dryness. Recrystallization of the residue from methanol-ethyl acetate gave the pure hydrochloride salt (m.p. 178°).

5.25 Grams (18 mmoles) of 1-(3'-thienyl)-7,8-dimethoxy-2,3,4,5-tetrahydro-3-1H-benzazepine dissolved in 90 ml of methylene chloride was cooled to −12° by means of a methanol/ice bath and 9 ml of boron tribromide (93 mmoles) was added dropwise. The resulting solution was allowed to warm to room temperature for 1.5 hours. The solvent was stripped off to give a brown residue which was chilled and carefully treated with methanol. The methanol was evaporated under reduced pressure and the resulting residue was again treated with methanol and stripped at 50°. This process was repeated 3 times and 4.2 g of crude 1-(3'-thienyl)-7,8-dihydroxy-2,3,4,5-tetrahydro-3-1H-benzazepine hydrobromide was obtained. This was further purified by chromatography over silica, eluted with 9:1 chloroform:methanol, and dissolved in water, charcoaled and filtered. Lyophilization of the filtrate gave 2.8 g of buff colored amorphous powder (m.p. 254-6° dec.).

$C_{14}H_{15}NO_2S \cdot HBr \cdot \frac{1}{4}H_2O$. Calculated: 46.10% C; 5.11% H; 3.84% N; 8.73% S. Found: 45.84% C; 4.89% H; 3.68% N; 8.39% S.

EXAMPLE 4

To 181 g (1 mole) of homoveratrylamine in 1 l. of ethanol was added 117 g (1.1 mole) of benzaldehyde. The mixture was stirred at room temperature for 15 minutes. A solution of 100 g of potassium borohydride in 500 ml cold water was then slowly added while the solution was kept at near room temperature by external cooling. After complete addition of the hydride solution, the reaction mixture was stirred for 5 hours and then chilled and acidified with 6 N hydrochloric acid. Further chilling to 0° precipitated the N-benzyl homoveratrylamine hydrochloric salt which was collected by filtration. The crude product recrystallized from ethanol (m.p. 204°-6°).

44 Grams (0.143 moles) of the N-benzylhomoveratrylamine hydrochloride salt was suspended in 440 ml of dry dimethylformamide. To this were added 100 g (0.725 moles) of powdered anhydrous potassium carbonate and 29 g (0.17 mole) of bromoacetaldehyde dimethyl acetal. The reaction mixture was heated at reflux with stirring for 20-24 hours under argon. The salts were then removed by filtration, and the filtrate was evaporated under reduced pressure to yield a dark brown oil. This was dissolved in a water-ethyl acetate mixture and the layers were separated. The water layer was thoroughly extracted with ethyl acetate. The combined organic layers were back washed once with brine solution, dried, and the solvent evaporated to give 46 g of crude product (brown syrup 90% yield). Chromatography gave a 64% yield of pure N-benzyl-N-($\beta$-3,4-dimethoxyphenyl)ethylaminoacetaldehyde dimethyl acetal.

The dimethyl acetal (24 g) was dissolved in 240 ml of conc. HCl:HOAc:H₂O (3:3:1 ratio) and allowed to stand overnight at room temperature. It was then poured into 1 l. ice-water, basified to pH=8 by addition of conc. ammonia, and extracted with ethyl acetate. The extracts were combined, back washed once with saturated brine and dried over anhydrous sodium sulfate. Removal of the drying agent and solvent gave 19.5 g of crude product (92% yield).

Chromatography over a silica column gave pure N-benzyl-1-hydroxy-7,8-dimethoxy-2,3,4,5-tetrahydro-1H-3-benzazepine in a 51% yield. The oily product could be crystallized from ethyl acetate-hexane.

The "dimethylacetal" reaction described in detail above is another general method which may be used to prepare various 1-hydroxybenzazepine intermediates of this invention using as starting materials various substituted N-lower alkyl or phenalkylhomoveratrylamines especially the N-methyl, N-benzyl or N-phenethylhomoveratrylamines. The reaction apparently does not go on the N-H amines. The N-benzyl compounds are of most general use because the protective benzyl group can be readily removed as described hereafter.

1.1 Grams of the pure N-benzyl-1-hydroxyl benzazepine was dissolved in 50 ml methanol and 220 mg 10% palladium on charcoal wetted with butanol was added. The solution was shaken for 4 hours under hydrogen at 40 psi. The catalyst was removed by filtration and the filtrate was evaporated under reduced pressure to give a slightly yellow syrup which was crystallized from ethyl acetate. Recrystallization from acetonitrile (m.p. 153°-4°) gave pure 1-hydroxy-7,8-dimethoxy-2,3,4,5-tetrahydro-1H-3-benzazepine a key new intermediate.

8.9 Grams (40 mmoles) of 1-hydroxy-7,8-dimethoxy-2,3,4,5-tetrahydro-1H-3-benzazepine and 2.5 ml of 2-methyl-thiophene were dissolved in 45 ml trifluoroacetic acid. The reaction mixture was allowed to stand at room temperature overnight, then evaporated under reduced pressure to an oily residue which was dissolved in 250 ml of 3 N hydrochloric acid. The acidic solution was thoroughly washed with ether, then basified with conc. ammonia, and finally extracted with ethyl acetate. The organic extracts were combined, washed with saturated brine, and dried over anhydrous sodium sulfate. Removal of drying agent and solvent gave 10.1 g. of 1-(5'-methyl-2'-thienyl)-7,8-dimethoxy-2,3,4,5-tetrahydro-1H-3-benzazepine as an oil (83.3%). In the same way 1-(2'-thienyl)-7,8-dimethoxy-2,3,4,5-tetrahydro-1H-3-benzazepine, and 1-(2'-furyl)-7,8-dimethoxy-2,3,4,5-tetrahydro-1H-3-benzazepine are made using thiophene, 2-bromothiophene and furan.

EXAMPLE 5

4.6 Grams (15 mmoles) of 1-(5'-methyl-2'-thienyl)-7,8-dimethoxy-2,3,4,5-tetrahydro-3-1H-benzazepine was dissolved in 45 ml methylene chloride under argon; the solution was cooled to $-12°$ by a methanol-ice bath, and 78 ml of boron tribromide in methylene chloride (1 g/5 ml) was slowly added. The dark brown solution which resulted was allowed to warm to room temperature for one hour, and evaporated under reduced pressure to a brown residue. This was chilled to 0°, methanol was slowly added and then evaporated. This was repeated 5 times and the resulting dark brown gum was dissolved in water and filtered through a pad of "Supercel". The filtrate was lyophilized to give a yellowish powder which was further purified by chromatography on silica gel. Elution with 9:1 chloroformmethanol gave 2.4 g of pure 1-(5'-methyl-2'-thienyl)-7,8-dihydroxy-2,3,4,5-tetrahydro-1H-3-benzazepine hydrobromide (m.p. 169° dec.).

$C_{15}H_{17}NO_2S \cdot HBR \cdot \frac{3}{4}H_2O$. Calculated: 48.72% C; 4.91% H; 3.78% N. Found: 48.86% C; 4.84% H; 3.87% N.

In similar manner the 7,8-dihydroxy-1-(2'-thienyl), (5'-bromo-2'-thienyl) and (2'-furyl) congeners are made from the 7,8-dimethoxy compounds of Example 4.

EXAMPLE 6

A mixture of 10.2 g (0.056 mole) of homoveratrylamine and 5.9 g (0.053 mole) of 2-epoxyethylfuran were mixed and heated on the steam bath overnight and worked up as in Example 1 to give N-(β-hydroxy-β-2'-furyl)ethylhomoveratrylamine, as a crystalline solid which was recrystallized from ethyl acetate-petroleum ether (m.p. 90°).

The furylaminoalcohol (2.9 g) was cyclized in 30 ml of trifluoroacetic acid at room temperature overnight. The black mixture was poured into 20 ml of ammonium hydroxide/300 ml of ice and 40 ml of ethyl acetate, and more ammonia was added to pH 9. The combined organic layer and subsequent extracts were washed with brine and dried over anhydrous sodium sulfate. Evaporation of the solvent in vacuo after removal of the drying agent gave 2.51 g of oily product, 1-(2'-furyl)-7,8-dimethoxy-2,3,4,5-tetrahydro-1H-3-benzazepine. This material is identical to the same product prepared by catalytic hydrogenation of the N-benzyl derivative (Examples 7 and 8) using palladium on charcoal in methanol at 50°.

EXAMPLE 7

A solution of 20.1 g (64 mmole) of 1-hydroxy-N-benzyl-7,8-dimethoxy-2,3,4,5-tetrahydro-1H-3-benzazepine in 130 ml of methylene chloride was treated with 14 g (0.2 mole) of furan and 16 ml of ethereal boron trifluoride. After standing overnight at room temperature the reaction mixture was stirred with concentrated ammonium hydroxide and ice. The methylene chloride phase was separated and extracted with 1 M phosphoric acid. The acid extracts were neutralized and extracted with ethyl acetate. The dried extracts were evaporated to 19.8 g of crude product [1-(2'-furyl)-3-benzyl-7,8-dimethoxy-2,3,4,5-tetrahydro-1H-3-benzazepine] which was purified by chromatography over silica.

EXAMPLE 8

The N-benzyl product (14.2 g, 0.12 mole), prepared as in Example 7, in methylene chloride was reacted with 145 ml of boron tribromide-methylene chloride (1 g/5 ml) at room temperature for 1.25 hours. The desired 1-(2'-furyl)-3-benzyl-7,8-dihydroxy-2,3,4,5-tetrahydro-1H-3-benzazepine was isolated as described above. This compound was debenzylated by hydrogenolysis as described in Example 6 to give 1-(2'-furyl)-3-benzyl-7,8,-dihydroxy-2,3,4,5-tetrahydro-1H-3-benzazepine was isolated as described above. This compound was debenzylated by hydrogenalysis as described in Example 6 to give 1-(2'-furyl)-7,8-dihydroxy-2,3,4,5-tetrahydro-1H-3-benzazepine. It's hemi-fumarate salt was prepared in methanol and was recrystallized from water (m.p. 267° dec.).

$C_{14}H_{15}NO_3 \cdot \frac{1}{2}C_4H_4O_4 \cdot \frac{1}{4}H_2O$. Calculated: 62.43% C; 5.73% H; 4.56% N. Found: 62.78% C; 6.14% H; 4.52% N.

EXAMPLE 9

Three solutions each with 0.31 g (1 mmole) of 1-hydroxy-3-benzyl-7,8-dimethoxy-2,3,4,5-tetrahydro-1H-3-benzazepine in 2 ml of methylene chloride containing boron trifluoride etherate were respectively reacted with an excess of furan, 2-methylfuran and 2-cyanomethylfuran at room temperature overnight. Each was quenched in ammonia solution, isolated and passed over silica gel. This layer chromatography on silica gel using cyclohexane-ethyl acetate (7:3) gave $R_f$ values of 0.68, 0.70 and 0.43 respectively with the starting material at 0.14. These are the 2'-furyl, 5'-methyl-2'-furyl and 5'-cyanomethyl-2'-furyl congeners which can be optionally debenzylated and demethylated as described to give 1-(2'-furyl)-7,8-dihydroxy-2,3,4,5-tetrahydro-1H-3-benzazepine, its methylfuryl and its cyanomethylfuryl congeners.

Repeating this reaction with 1-hydroxy-3-methyl-7,8-dimethoxy-2,3,4,5-tetrahydro-1H-3-benzazepine (prepared from N-methylhomoveratrylamine as in Example 4 and 2-methylthiophene gives 1-(5'-methyl-2'-thienyl)-3-methyl-7,8-dimethoxy-2,3,4,5-tetrahydro-1H-3-benzazepine. Demethylation as described above gives 1-(5'-methyl-2'-thienyl)-3-methyl-7,8-dihydroxy-2,3,4,5-tetrahydro-1H-3-benzazepine hydrobromide.

EXAMPLE 10

A mixture of 7.9 g (25.2 mmoles) of 1-hydroxy-3-benzyl-7,8-dimethoxy-2,3,4,5-tetrahydro-1H-3-benzazepine, 6.35 g (50.4 mmoles) of methyl furoate and 6.2 ml (50.4 mmoles) of boron trifluoride etherate was reacted at room temperature for 1.5 hours. Another 3.1 ml of trifluoride was added followed by standing at room temperature overnight. The product, 1-(5'-carbomethoxy-2'-furyl)-benzyl-7,8-dimethoxy-2,3,4,5-tetrahydro-1H-3-benzazepine was isolated and purified by methods similar to those of the previous examples. This material was demethylated to the 7,8-dihydroxy compound and debenzylated as described above to give 1-(5'-carbomethoxy-2'-furyl)-7,8-dihydroxy-2,3,4,5-tetrahydro-1H-3-benzazepine hemifumarate hydrate, m.p. 198°–200° (dec.):

EXAMPLE 11

Reacting 2-chloro-3,4-dimethoxyphenylethylamine, 2-fluoro-3,4-dimethoxyphenylethylamine or 2-trifluoromethyl-3,4-dimethoxyphenylethylamine (prepared via 2-trifluoromethyl-3,4-dimethoxytoluene) in a stoichiometric quantities with 2-epoxyethylthiophene as in Example 1 gives 2-chloro-1-(2'thienyl)-7,8-dihydroxy-2,3,4,5-tetrahydro-1H-3-benzazepine, 6-fluoro-1-(2'-thienyl)-7,8-dihydroxy-2,3,4,5-tetrahydro-1H-3-benzazepine and 6-trifluoromethyl-1-(2'-thienyl)'7,8-dihydroxy-2,3,4,5-tetrahydro-1H-3-benzazepine via their 7,8-dimethyl ethers.

EXAMPLE 12

A mixture of 4.5 g of 6-chloro-7,8-dimethoxy-1-(2'-thienyl)-2,3,4,5-tetrahydro-1H-3-benzazepine, 0.02 ml of n-butyl bromide and 0.02 mol of potassium hydroxide is dissolved in 120 ml of dry methanol and refluxed for 48 hours. The reaction mixture is evaporated to dryness, taken up in ethyl acetate and filtered to remove inorganic salts. The filtrate is washed with water, dried and evaporated to give 3-n-butyl-6-chloro-7,8-dimethoxy-1-(2'-thienyl)-2,3,4,5-tetrahydro-1H-3-benzazepine.

The 3-n-butyl benzazepine (0.01 mol) is dissolved in 120 ml of dry methylene chloride and 0.032 mol of boron tribromide is added dropwise at −10°. The solution is warmed to room temperature and stirred for two hours. The excess boron tribromide is destroyed with methanol added dropwise with ice-cooling. The cold solution is refluxed on the steam bath to remove hydrogen bromide and evaporated. The residue is treated with brine at reflux for 2 hours to yield 3-n-butyl-6-chloro-7,8-dihydroxy-1-(2'-thienyl)-2,3,4,5-tetrahydro-1H-3-benzazepine hydrobromide.

Using N-alkylation procedures described above but using 7,8-dimethoxy-1-(5'-methyl-2'-thienyl)-2,3,4,5-tetrahydro-1H-3-benzazepine as a model compound the N-allyl, N-phenethyl, N-butyl, N-amyl or N-2,2-dimethylallyl derivatives are prepared. Hydrolysis of the methoxy groups as described gives the active 7,8-dihydroxy compounds.

EXAMPLE 13

A 3.9 g sample of 7,8-dihydroxy-1-(3'-thienyl)-2,3,4,5-tetrahydro-1H-3-benzazepine is slurried in 25 ml of acetone and 0.7 g (0.016 mol, 10% excess) of ethylene oxide is added. The mixture is placed in a pressure bottle and stirred at ambient temperature for about 40 hours. The reaction mixture is then heated to 60°–80° for 30 minutes, cooled and filtered. Concentration of the filtrate gives a solid which is taken up in ethyl acetate and reprecipitated with ether. The solid thus obtained is dissolved in ethanol and treated with ethereal hydrogen chloride to give 7,8-dihydroxy-3-(2-hydroxyethyl)-1-(3'-thienyl)-2,3,4,5-tetrahydro-1H-3-benzazepine hydrochloride.

EXAMPLE 14

A 4.0 g sample of 3-benzyl-7,8-dihydroxy-1-(2'-thienyl)-2,3,4,5-tetrahydro-1H-3-benzazepine (prepared from the 3-unsubstituted benzazepine by reaction with benzyl bromide in the presence of potassium carbonate) is dissolved in 50 ml of acetic anhydride and the solution is heated on a steam bath for one hour. The reaction mixture is cooled, ice-water is added and the solution is evaporated to dryness. The residue is triturated with ethyl acetate, the solution washed with water, dried and the solvent removed in vacuo to leave an oil. The latter is dissolved in ether and ethereal hydrogen chloride is added to precipitate 3-benzyl-7,8-diacetoxy-1-(2'thienyl)-2,3,4,5-tetrahydro-1H-3-benzazepine hydrochloride.

7,8-dihydroxy-1-(2'-thienyl)-2,3,4,5-tetrahydro-1H-3-benzazepine hydrobromide (10 g) is dissolved in trifluoroacetic acid and reacted with a stoichiometric amount of acetyl bromide at room temperature for 1–2 hours. The reaction mixture is evaporated and the residue is triturated in ether-i-propanol to give the desired diacetoxy derivative.

Substituting other alkanoy anhydrides or chlorides gives various 7,8-alkanoyl derivatives such as the diacetoxy derivatives of 2'-furyl, 5'-methyl-2'-furyl, 5'-cyanomethyl, 3'-thienyl, 5'-methyl-2'-thienyl, and 5'-bromo-2'-thienyl compounds.

EXAMPLE 15

7,8-Dihydroxy-1-(2'-thienyl)-2,3,4,5-tetrahydro-1H-3-benzazepine (5 g) is suspended in 500 cc of benzene. Trifluoroacetic anhydride (15 g) is added dropwise rapidly. The solution is stirred an additional hour and the volatiles stripped off, leaving the N,O,O-tris-trifluoroacetyl derivative. This is added directly to 500 cc of methanol and hydrogen chloride gas bubbled in for a few minutes. The reaction is stirred for 2 hours and then the solvent stripped off, leaving 7,8-dihydroxy-1-(2'-thienyl)-3-trifluoroacetyl-2,3,4,5-tetrahydro-1H-3-benzazepine.

EXAMPLE 16

Dry dimethylformamide (50 ml) is deoxygenated four times by pulling a vacuum and refilling the vacuated flask with argon. 7,8-Dihydroxy-1-(2'-thienyl)-3-trifluoroacetyl-2,3,4,5-tetrahydro-1H-3-benzazepine (5 g) is added and dissolved as the solution is deoxygenated once more. Methylene bromide (5.3 g) potassium carbonate (5 g) and cupric oxide (0.13 g) are added and the solution is deoxygenated a final time. The reaction is heated at 150° under argon for 2 hours.

It is worked up by pouring into 2 l. of ice water while stirring. The aqueous suspension is extracted four times with 300–400 cc ether, and the ether is back extracted three times with 1.5 l. water. The ether is dried and evaporated. The residue is dissolved in chloroform and chromatographed on silica gel to give 7,8-methylenedioxy-1-(2'-thienyl)-3-trifluoroacetyl-2,3,4,5-tetrahydro-1H-3-benzazepine.

EXAMPLE 17

A suspension of 7,8-dihydroxy-1-(2'-thienyl)-2,3,4,5-tetrahydro-1H-3-benzazepine hydrobromide (3.4 g) in methanol (40 ml) is reacted with 2.5 g of 2,3-dichloro-5,6-dicyano-1,4-benzoquinone in methanol at 0° for 1 hour. The 1-(2'-thienyl)-2,3,4,5-tetrahydro-1H-3-benzazepine-7,8-dione hydrobromide was collected by filtration and washed with ether. The dione hydrobromide salt is added to an excess of methyl mercaptan in methanol. After 1 hour the solution is evaporated to give a residue of the 6-methylthio and 9-methylthio isomers. Separation over a silica gel column gives 6-methylthio-1-(2'-thienyl)-2,3,4,5-tetrahydro-1H-3-benzazepine hydrobromide salt.

Similarly 6-methylthio-3'-thienyl and 2'-furyl congeners are made.

EXAMPLE 18

5.5 Grams (18 mm) of 7,8-dimethoxy-1-(5'-methyl-2'-thienyl-2,3,4,5-tetrahydro-1H-3-benzazepine was dissolved in 120 ml of ethylformate and was heated at reflux for 24 hours. After addition of 50 ml of ethyl ether, the reaction mixture was washed with 3×30 ml of 3 N hydrochloric acid, 2×20 ml of 5% sodium bicarbonate, and then brine. After drying over sodium sulfate and removal of the drying agent, the solvent was evaporated to give 4.8 g of the oily N-formyl derivative.

EXAMPLE 19

To 120 ml of ethyl ether under argon, 2.15 g of lithium aluminum hydride was added followed by addition of 4.7 g (14.2 mmoles) of the N-formyl derivative in 80 ml of benzene. The resulting suspension was gently refluxed for 5 hours. It was then cooled and the excess hydride was decomposed by addition of 6 ml of methanol in 25 ml ether, 2.15 ml of water, 2.15 ml of 10% alkali, and 6.45 ml of water, in that sequence. The solid formed was removed by filtration. The filtrate was evaporated to an oil which was taken up in ethyl acetate and thoroughly extracted with 3 N hydrochloric acid. The acidic extracts were combined, washed with ether, basified to pH 8, and thoroughly extracted with ethyl acetate. The organic extracts were combined and dried over anhydrous sodium carbonate. Removal of the drying agent and solvent gave 3.6 g of 1-(5'-methyl-2-thienyl)-3-methyl-7,8-dimethoxy-2,3,4,5-tetrahydro-1H-3-benzazepine.

This was dissolved in methanol and ethereal hydrogen chloride was added. The solution was stripped to dryness under reduced pressure to give 7,8-dimethoxy-1-(5'-methyl-2'-thienyl)-3-methyl-2,3,4,5-tetrahydro-1H-3-benzazepine which was recrystallized from methanol-ethyl acetate hydrochloride (m.p. 227°–8°).

Substituting the 1-(2'-thienyl), 1-(3'-thienyl) or 1-(2'-furyl) congeners in the procedures of Examples 19–20 with obvious variations gives 7,8-dimethoxy-1-(2'-thienyl)-3-methyl-3,3,4,5-tetrahydro-1H-3-benzazepine hydrochloride, 7,8-dimethoxy-1-(3'-thienyl)-3-methyl-2,3,4,5-tetrahydro-1H-3-benzazepine hydrochloride or 7,8-dimethoxy-1-(2'-furyl)-3-methyl-2,3,4,5-tetrahydro-1H-3-benzazepine hemifumarate. Splitting the ethers as described above gives the three dihydroxy congeners.

EXAMPLE 20

Treatment of the dione hydrobromide salt with anhydrous hydrogen bromide in methylene chloride or with diluted hydrobromic acid, gives 6-bromo-1-(2'-thienyl)-2,3,4,5-tetrahydro-1H-3-benzazepine hydrobromide salt. Similarly the 6-bromo-1-(5'-methyl-2'-thienyl), 6-bromo-1-(2'-furyl), 6-bromo-3'-thienyl analogs are prepared.

| Ingredients | Mg. per Capsule |
|---|---|
| 7,8-Dihydroxy-1-(5'-methyl-2'-thienyl)-2,3,4,5-tetrahydro-1H-3-benzazepine (as an acid addition salt) | 125 (free base) |
| Magnesium stearate | 2 |
| Lactose | 200 |

The above ingredients are thoroughly mixed and placed into hard gelatin capsules. Such capsules are administered orally to subjects in need of treatment from 1–5 times daily to induce dopaminergic activity.

EXAMPLE 21

| Ingredients | Mg. per Tablet |
|---|---|
| 7,8-Dihydroxy-1-(2'-thienyl)-2,3,4,5-tetrahydro-1H-3-benzazepine (as an acid addition salt) | 200 (free base) |
| Corn starch | 30 |
| Polyvinyl pyrrolidone | 12 |
| Corn starch | 16 |
| Magnesium stearate | 3 |

The first two ingredients are thoroughly mixed and granulated. the granules obtained are dried, mixed with the remaining corn starch and magnesium stearate, and compressed into tablets.

The capsules or tablets thusly prepared are administered orally to an animal or human requiring stimulation of either peripheral or central dopamine receptors to induce hypotension or to treat the symptoms of Parkinson's disease within the dose ranges set forth hereinabove. Similarly other compounds of Formula I and the illustrative examples can be formulated in the same manner to give pharmaceutical compositions useful in the methods of this invention based on the chemical characteristics and relative biological activity using the test methods outlined.

What is claimed is:

1. A compound of the formula:

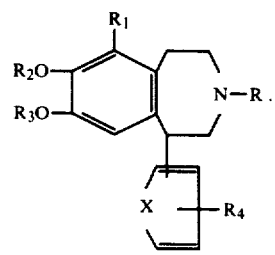

in which:

R is hydrogen, benzyl, phenethyl, lower alkanoyl of 1–5 carbons, lower alkyl of 1–5 carbons, hydroxyethyl or lower alkenyl of 3–5 carbons;

$R_1$ is hydrogen, halo, trifluoromethyl, methylthio, trifluoromethylthio, methyl or methoxy;

$R_2$ and $R_3$ are hydrogen;

$R_4$ is hydrogen, halo, cyanomethyl or methyl; and

X is —O—; and the pharmaceutically acceptable nontoxic salts thereof.

2. The compound of claim 1 in which R is hydrogen or methyl, $R_1$ is hydrogen or chloro, $R_2$ and $R_3$ are hydrogen; and $R_4$ is hydrogen or methyl.

3. The compound of claim 1 in which R, $R_1$, $R_2$, $R_3$ and $R_4$ are hydrogen.

4. The compound of claim 3 in which the furyl ring is attached at the 2'-position.

5. The compound of claim 4 in which the salt form is the hydrobromide.

6. The method of inducing dopaminergic activity in an animal or human subject in need thereof comprising administering orally or by injection an effective and nontoxic quantity of a compound of claim 1.

7. A pharmaceutical composition having dopaminergic activity comprising an effective therefor and nontoxic quantity of a compound of claim 1 and a dosage unit carrier therefor.

* * * * *